United States Patent
Liu et al.

(10) Patent No.: US 8,962,895 B2
(45) Date of Patent: Feb. 24, 2015

(54) METHOD FOR THE PRODUCTION OF ETHYLENE GLYCOL

(75) Inventors: Juntao Liu, Shanghai (CN); Weimin Yang, Shanghai (CN); Lei Li, Shanghai (CN); Wanmin Wang, Shanghai (CN); Linna Zhang, Shanghai (CN); Haifeng Song, Shanghai (CN)

(73) Assignees: China Petroleum & Chemical Corporation, Beijing (CN); Shanghai Research Institute of Petrochemical Technology, Sinopec, Shanghai (CN)

( * ) Notice: Subject to any disclaimer, the term of this patent is extended or adjusted under 35 U.S.C. 154(b) by 48 days.

(21) Appl. No.: 14/001,120

(22) PCT Filed: Feb. 24, 2012

(86) PCT No.: PCT/CN2012/000237
§ 371 (c)(1),
(2), (4) Date: Aug. 22, 2013

(87) PCT Pub. No.: WO2012/113268
PCT Pub. Date: Aug. 30, 2012

(65) Prior Publication Data
US 2013/0338406 A1    Dec. 19, 2013

(30) Foreign Application Priority Data

Feb. 25, 2011 (CN) .......................... 2011 1 0045625
Feb. 25, 2011 (CN) .......................... 2011 1 0046339

(51) Int. Cl.
C07C 29/149    (2006.01)
B01J 8/06      (2006.01)

(52) U.S. Cl.
CPC .............. *C07C 29/149* (2013.01); *B01J 8/067* (2013.01); *B01J 2208/0053* (2013.01)
USPC .......................................................... 568/864

(58) Field of Classification Search
CPC .................................................... C07C 29/149

USPC .......................................................... 568/864
See application file for complete search history.

(56) References Cited

U.S. PATENT DOCUMENTS

| 4,649,226 A | 3/1987 | Poppelsdorf et al. |
| 2010/0179356 A1 | 7/2010 | Liu et al. |

FOREIGN PATENT DOCUMENTS

| CN | 101138725 A | 3/2008 |
| CN | 101475441 A | 7/2009 |
| CN | 101475442 A | 7/2009 |
| CN | 101934210 A | 1/2011 |
| DE | 2123950 A1 | 11/1972 |

OTHER PUBLICATIONS

International Search Report (PCT/ISA/210) issued on May 31, 2012, by the China Patent Office as the International Searching Authority for International Application No. PCT/CN2012/000237.
Tang, B. et al., "Study on the Catalysts for Hydrogenation of Dimethyl Oxalate to Ethylene Glycol", Chinese Journal of Spectroscopy Laboratory, vol. 27, No. 2, pp. 616-619 (Mar. 2010) (with English abstract).

*Primary Examiner* — Elvis O Price
(74) *Attorney, Agent, or Firm* — Buchanan Ingersoll & Rooney PC

(57) ABSTRACT

The present invention relates to a method for the production of ethylene glycol using a feedstock comprising an oxalate and a catalyst containing copper and/or a copper oxide, comprising contacting the feedstock with the catalyst in a reactor under the conditions of a temperature in the range from about 170 to about 270° C., a weight hourly space velocity of the oxalate in the range from about 0.2 to about 5 $h^{-1}$, a molar ratio of hydrogen to the oxalate in the range from about 40:1 to about 200:1 and a reaction pressure in the range from about 1.5 to about 10 MPa, to produce an effluent containing ethylene glycol, in which the reactor is a tube-array reactor using partitioned heat exchange and adopting outer and inner tubes configured in a double-tube structure to facilitate the heat exchange of the catalyst.

18 Claims, 1 Drawing Sheet

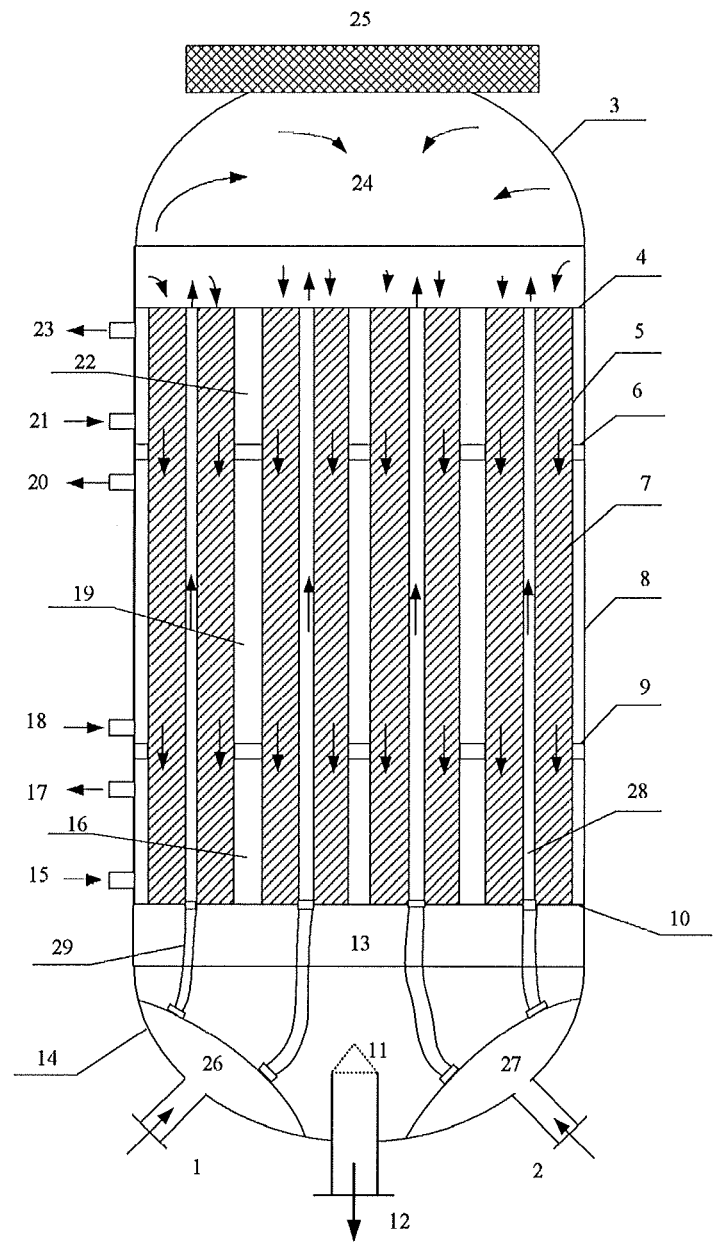

METHOD FOR THE PRODUCTION OF ETHYLENE GLYCOL

TECHNICAL FIELD

The present invention relates to a highly efficient method for producing ethylene glycol, especially to a method for producing ethylene glycol by hydrogenating dimethyl oxalate or diethyl oxalate in a tube-array reactor using partitioned heat exchange and adopting outer and inner tubes configured in a double-tube structure favourable for heat exchange.

BACKGROUND ART

Ethylene glycol (EG) is an important and widely used raw material in organic chemical industries. Ethylene glycol is mainly used for producing polyacetate fibers, antifreezing agents, unsaturated polyester resins, lubricants, plasticizers, non-ionic surfactants and explosives. Furthermore, ethylene glycol also can be used in many fields including paint, photographic developer, brake fluid, ink and the like, used as a solvent and medium for ammonium perborate, and used for producing special solvents such as glycol ether.

At present, China has surpassed the United States to become the largest ethylene glycol consumer in the world. The average annual growth rate of apparent domestic ethylene glycol consumption from 2001 to 2006 is 17.4%. Although China's ethylene glycol production capacity and output are growing rapidly, the increasing market demand still cannot be satisfied due to the strong development of related industries such as the polyester industry. A large number of ethylene glycol has to be imported every year and its import quantity is increasing year by year.

Currently, large domestic and foreign ethylene glycol producers adopt a direct hydration of ethylene oxide, i.e. the pressured hydration process, for the commercial production of ethylene glycol. This production process is only grasped by three companies, Royal Dutch/Shell Group, Halcon-SD, U.S.A. and UCC, U.S.A. In addition, the research and development of new synthesis processes of ethylene glycol are still progressing. By way of example, Shell, UCC, Moscow Mendeleev Institute of Chemical Process, Shanghai Petrochemical Institute and others have developed an ethylene glycol production process involving the catalytic hydration ethylene oxide; Halcon-SD, UCC, Dow Chemical, Japan Catalysis Chemical, Mitsubishi Chemical and others have developed a process for producing ethylene glycol from ethylene carbonate; and Dow Chemical and others have developed a process for producing ethylene glycol via a coproduction of EG and dimethyl carbonate (DMC).

As for the direct hydration method, due to the high water content of the reaction product, the subsequent equipment (i.e. evaporator) needs an extended processing procedure, a large size and a high energy consumption and the total yield of the process is only about 70%, which has directly impacted the cost for the production of ethylene glycol. In comparison with the direct hydration method, the catalytic hydration method can greatly reduce the water content of the reaction product, and increase the conversion of the feedstock and the EG selectivity. If the catalyst stability problem and related engineering and technical problems could be solved successfully, the replacement of the non-catalytic hydration process with the catalytic hydration process in EG production would be irresistable. Ethylene carbonate (EC)-to-EG production process is superior over the EC direct hydration method in the conversion of feedstock, EG selectivity and the consumption of feedstock and energy, and thus is an advanced method. The EG and DMC coproduction process can make full use of the $CO_2$ by-product of the ethylene oxidation process, so that two high valuable products can be produced in existing EC production plant by simply adding a reaction step for producing EC, which is very attractive.

However, the above-described methods share a common drawback of the consumption of ethylene, which is mainly derived from traditional petroleum refining at present. Since the high global petroleum price will be sustained for a long period in the future, the route for production of ethylene glycol from abundant and cheap natural gas or coal instead of petroleum (non-petroleum route, also known as CO route) becomes a competitive one for the traditional ethylene route. Among others, new techniques for the production of EG from syngas may have great influence on the innovation of EG production processes. A very attractive route in coal chemical industry for the production of EG is to produce dimethyl oxalate by using CO as a starting material and subsequently convert dimethyl oxalate into EG via hydrogenation. By far, the study at home and abroad on the production of dimethyl oxalate from CO has yielded good results, and a mature industrial production process has been developed. However, as for the hydrogenation of dimethyl oxalate to EG, there is still a lot of work to do in research. In particular, there is still no breakthrough in the study on how to effectively improve the selectivity to ethylene glycol and improve the stability of the catalyst.

It is disclosed in Spectroscopy Laboratory, 2010, 27 (2), pages 616-619, a hydrogenation catalyst useful for producing ethylene glycol from dimethyl oxalate, which is a Cu—B/$\gamma$-$Al_2O_3$ or Cu—B/$SiO_2$ amorphous alloy catalyst prepared by chemical reduction deposition and the evaluation of which shows a low oxalate conversion and an EG selectivity of less than 90%.

It is disclosed in CN200710061390.3 a hydrogenation catalyst useful for the synthesis of ethylene glycol from an oxalate and the preparation thereof, with which the oxalate conversion achieved is relatively low, typically about 96%, and the EG selectivity achieved is about 92%.

The main problem present in the above documents lies in the low EG selectivity, which still needs to be enhanced and improved.

SUMMARY OF THE INVENTION

The technical problem to be solved by the present invention is the problem of low EG selectivity present in prior arts. A new efficient method for producing ethylene glycol is provided, which has the benefit of high EG selectivity.

In order to solve the above technical problem, the present invention provides a method for the production of ethylene glycol using a feedstock comprising an oxalate and a catalyst containing copper and/or a copper oxide, which comprises contacting the feedstock with the catalyst in a reactor under the conditions of a temperature in the range from about 170 to about 270° C., a weight hourly space velocity of the oxalate in the range from about 0.2 to about 7 $h^{-1}$, a molar ratio of hydrogen to the oxalate in the range from about 20:1 to about 200:1 and a reaction pressure in the range from about 1.5 to about 10 MPa, to produce an effluent containing ethylene glycol, in which the reactor is a tube-array reactor using partitioned heat exchange and adopting outer and inner tubes configured in a double-tube structure to facilitate the heat exchange of the catalyst.

As used herein, "partitioned heat exchange" means that the reactor has at least two heat-exchange zones and the temperature of each heat-exchange zone can be individually controlled so as to achieve an accurate control of the temperature of the region to be heated or cooled and to achieve a uniform distribution of the temperature in the catalyst bed.

As used herein, "adopting outer and inner tubes configured in a double-tube structure" means that the reaction tube used in the reactor consists of an inner tube and an outer tube. A solid catalyst is packed within the annular space between the inner tube and the outer tube. The inner tube is a channel for a gaseous feedstock to be preheated and to undergo a heat-exchange. The space out of the outer tube is a flow channel for a heat-exchange medium. The double-tube structure of the inner and outer tubes allows a lower temperature difference within the catalyst bed, allowing an approximately isothermal reaction to occur, which advantageously guarantees the optimal reaction performance of the catalyst. In the above mentioned technical solution, preferred reaction conditions in the reactor are as follows: a reaction temperature in the range from about 180 to about 260° C., a weight hourly space velocity of the oxalate in the range from about 0.3 to about 3 $h^{-1}$, a molar ratio of hydrogen to the oxalate in the range from about 50:1 to about 150:1, and a reaction pressure in the range from about 2.0 to about 6.0 MPa. In a preferred embodiment, the catalyst comprises, based on the total parts by weight of the catalyst, about 5 to about 80 parts of the copper and/or copper oxide as an active ingredient, about 10 to about 90 parts of at least one of silica, molecular sieve or alumina as a support material, and about 0.01 to about 30 parts of a metal selected from niobium, cerium, bismuth and tungsten or a oxide thereof as an auxiliary agent. In a more preferred embodiment, the catalyst comprises, based on the total parts by weight of the catalyst, about 10 to about 60 parts of the copper and/or copper oxide as the active ingredient, about 15 to about 90 parts of at least one of silica or alumina as the support material, and about 0.05 to about 20 parts of a metal selected from niobium, cerium, bismuth, tungsten, barium, silver and manganese or a oxide thereof as the auxiliary agent.

According to an embodiment of the present invention, the catalyst involved in the present invention has a pore volume in the range from about 0.1 to about 1 ml/g, preferably about 0.15 to about 0.8 ml/g, and an average pore diameter in the range from about 2 to about 12 nm, preferably about 3 to about 12 nm.

According to an embodiment of the present invention, the catalyst involved in the present invention has a specific surface area in the range from about 100 to about 400 $m^2/g$, preferably in the range from about 150 to about 380 $m^2/g$.

According to an embodiment of the present invention, the catalyst involved in the present invention has a crushing strength in the range from about 40 to about 180 N/cm, preferably in the range from about 40 to about 120 N/cm.

The reactor involved in the present invention comprises one or more sets of inner and outer tubes configured in the double-tube structure, with the total number of the reaction tube having inner and outer tubes configured in the double-tube structure accounting for about 5 to about 100 percent of the total number of all reaction tubes in the reactor, preferably about 30 to about 100 percent, more preferably about 50 to about 100 percent; and at least two heat-exchange zones, such as about 2 to about 40, and preferably about 3 to about 10.

The higher the ratio of the reaction tubes having the double-tube structure to overall reaction tubes in the reactor is, more uniform the axial temperature distribution within the catalyst will be. Since the oxalate hydrogenation reaction has a narrow temperature window, more uniform the temperature distribution is, the less the byproducts of the reaction and the higher the EG selectivity will be.

The more the number of the heat-exchange zones is, more accurately the temperature of the catalyst in the reactor can be controlled. Since the oxalate hydrogenation reaction is an exothermic reaction, normally hot-spots will form in the reaction zone. The individually controllable heat-exchange zone configuration of the present invention further allows the hot-spots to be "flatten", thereby improving the selectivity and yield more efficiently.

According to an embodiment of the present invention, the reactor involved in the present invention is mainly composed of a feedstock inlet, a feedstock inlet, a primary gas distribution chamber, a primary gas distribution chamber, a secondary gas distribution chamber, a bundle of reaction tubes comprising one or more sets of outer and inner tubes, a catalyst bed, a gas collecting chamber, a porous gas-collecting plate and a product outlet, in which the catalyst bed is divided into a first heat-exchange zone, a second heat-exchange zone and a third heat-exchange zone along the flow direction of the reaction gas; the first heat-exchange zone is connected with a first heat-exchange medium outlet and a first heat-exchange medium inlet; the second heat-exchange zone is connected with a second heat-exchange medium outlet and a second heat-exchange medium inlet; and the third heat-exchange zone is connected with a third heat-exchange medium outlet and a third heat-exchange medium inlet.

According to an embodiment of the present invention, the inner tube(s) is arranged within the catalyst bed and connected to the primary gas distribution chamber and the primary gas distribution chamber located in the gas collecting chamber via a gas inlet connecting hose. The porous gas-collecting plate is located in the gas collecting chamber and connected to the product outlet. The first and second heat-exchange zones are separated by a first partitioning plate, and the second and third heat-exchange zones are partitioned by a second partitioning plate.

The oxalate hydrogenation reaction is characterized in that, during the reaction, the radial temperature profile along the catalyst bed is normally lower at the inlet, increases gradually within a distance along the bed until reaches a higher hotspot temperature, and then decreases gradually along the reactor. In the region at the hotspot temperature, the reaction is relatively more vigorous, and the temperature is relatively higher, resulting in a lower EG selectivity and more side reactions. According to the above reaction characteristics, the temperature of the hotspot region can be adjusted to a temperature within the optimal reaction temperature range by optimizing the position for the partition of the heat-exchange zones, especially by individually conducting the heat exchange of the hotspot region, i.e. heat removing. Thus, the temperature difference within the bed of the reactor can be reduced, and the ratio of the catalyst having a temperature within the optimal reaction temperature range can be increased, and then the selectivity and yield of ethylene glycol can be improved and the utilization ratio of the feedstock can be increased.

According to an embodiment of the present invention, the first partitioning plate is located below the cover plate of the reactor with a distance therefrom in the range from about 1/12 to about 1/3, and preferably about 1/10 to about 1/3 of the length of the reactor.

According to an embodiment of the present invention, the second partitioning plate is located below the first partitioning plate with a distance therefrom in the range from about 1/12 to about 1/3, preferably about 1/10 to about 1/3 of the length of the reactor.

According to an embodiment of the present invention, the first partitioning plate is located below the cover plate of the reactor with a distance therefrom in the range from about $1/10$ to about $1/3$, and even preferably about $1/8$ to about $1/3$ of the length of the reactor; and the second partitioning plate is located below the first partitioning plate with a distance therefrom in the range from about $1/10$ to about $1/3$, and even preferably about $1/8$ to about $1/3$ of the length of the reactor.

Reaction rate of the catalytic reaction carried out over the catalyst is not constant along the catalyst bed. The reaction rate is generally high in the start portion of the reactor where the reaction is far from the equilibrium, releasing more reaction heat. In contrast, in the end portion of the reactor where the reaction is close to the equilibrium, the reaction rate is slowed, releasing less reaction heat. If a coolant with the same temperature is used, it will be difficult to achieve an optimal situation where the reaction is carried out at the optimal reaction temperature throughout the reactor. In particular, if the heat removement demand of the start portion of the reactor with higher reaction rate and more reaction heat is satisfied by reducing the temperature of the coolant to increase the temperature difference of heat exchange and heat removement, the reaction heat in the end portion of the reactor with less reaction heat will be insufficient so that the removed heat will be greater than the reaction heat generated, and thus the reaction temperature therein will be reduced causing a further slowdown of the reaction rate, and where the reaction temperature is below the active temperature of the catalyst, the catalytic reaction will stop. The present invention aims at solving this fundamental problem and utilizes coolants with different temperatures in different portions of the reactor instead of a coolant with the same temperature. In this way, the heat exchange during the reaction can be designed according to the reaction heat required to be removed. Particularly, the catalyst bed can be divided into several zones along the flow direction of the reaction gas therein and an indirect heat exchange is carried out with the coolant by means of a heat-exchange tube. In another aspect, the present invention further provides inner tubes in the catalyst bed and allows the gaseous feedstock to flow therein in a reverse direction. In this way, the energy consumption can be reduced by preheating the gaseous feedstock with the reaction heat from the catalyst, and meanwhile the temperature distribution across the catalyst bed can be optimized. Thus, a balanced temperature distribution throughout the catalyst bed can be achieved, which is advantageous for maximizing the efficiency of the catalyst, minimizing the loss of the oxalate and improving the selectivity to ethylene glycol.

According to an embodiment of the present invention, a superior technical effect can be achieved by contacting and reacting the feedstock comprising the oxalate with the catalyst containing a copper oxide in the device shown in FIG. 1 using partitioned heat exchange to achieve an accurate temperature control and adopting inner and outer tubes configured in the double-tube structure to facilitate the heat exchange of the catalyst under the conditions of a temperature in the range from about 160 to about 260° C., a reaction pressure in the range from about 1.0 to about 8.0 MPa, a molar ratio of hydrogen to the oxalate in the range from about 20:1 to about 200:1, an reaction space velocity in the range from about 0.1 to about 7 $h^{-1}$, to produce an effluent containing ethylene glycol, in which the conversion of the oxalate can reach 100%, and the EG selectivity can be greater than 95%.

BRIEF DESCRIPTION OF THE DRAWINGS

FIG. 1 is a schematic view of a reactor used in the method for producing ethylene glycol according to the present invention.

In FIG. 1, 1 and 2 are feedstock inlets; 3 is an upper head of the reactor; 4 is an upper tube plate; 5 is an outer tube in the bundle of reaction tubes; 6 is a first partitioning plate; 7 is a catalyst bed; 8 is a reactor tank; 9 is a second partitioning plate; 10 is a lower tube plate; 11 is a porous gas-collecting plate; 12 is a product outlet; 13 is a gas collecting chamber; 14 is a lower head of the reactor; 15 is a third heat-exchange medium inlet; 16 is a third heat-exchange zone; 17 is a third heat-exchange medium outlet; 18 is a second heat-exchange medium inlet; 19 is a second heat-exchange zone; 20 is a second heat-exchange medium outlet; 21 is a first heat-exchange medium inlet; 22 is a first heat-exchange zone; 23 is a first heat-exchange medium outlet; 24 is a secondary gas distribution chamber; 25 is a cover plate of the reactor; 26 and 27 are primary gas distribution chambers; 28 is an inner tube in the bundle of reaction tubes; and 29 is an gas inlet connecting hose.

In FIG. 1, the feedstock is introduced via feedstock inlets 1 and 2, and passed through the primary gas distribution chambers 26 and 27, respectively, and then directed into the inner tube 28 in the bundle of reaction tubes via the gas inlet connecting hose 29. After exchanging heat with the reaction heat in the catalyst bed 7, the feedstock is directed into the secondary gas distribution chamber 24, and then into the catalyst bed 7 located between the outer tube 5 and the inner tube 28 in the bundle of reaction tubes to contact and react with the catalyst. The resulted reaction product is directed into the gas collecting chamber 13, passed through the porous gas-collecting plate 11, and then withdrawn through the product outlet 12 to a subsequent system. While flowing through the first heat-exchange zone 22, the second heat-exchange zone 19 and the third heat-exchange zone 16 sequentially, the gaseous feedstock entering the catalyst bed 7 located between the outer tube 5 and the inner tube 28 in the bundle of reaction tubes contacts and reacts with the catalyst to release reaction heat. The temperature of each heat-exchange zone can be individually controlled by adjusting the temperature, flow rate and the like of the heat-exchange medium introduced thereinto. In addition, the heat equilibrium in the catalyst bed can be substantially facilitated by the counter-current contact of the gaseous feedstock within the inner tube 28 with the reaction gas within the catalyst bed, so that a uniform temperature distribution throughout the catalyst bed of the reactor can be achieved.

The present invention will be further illustrated with reference to the following examples, however the present invention is not limited to these examples.

DESCRIPTION OF PREFERRED EMBODIMENTS

EXAMPLE 1

A catalyst comprising 20 parts of Cu, 5 parts of Bi and 2 parts of W, based on the total parts by weight of the catalyst, was prepared by using silica having a specific surface area of 150 $m^2/g$ as the support material according to the following procedure: a) a solution of mixed nitrates of Cu, Bi and W (purchased from Shanghai Guoyao Group, 99.9% purity, the same below) and a solution of sodium carbonate (purchased from Shanghai Guoyao Group, 99.9% purity, the same below) with the desired concentration were prepared; b) the above solutions were co-precipitated at 70° C. with continuous stirring, and the pH value was 6 at the end of the precipitation; c) the precipitated slurry was washed with deionized water repeatedly until no $Na^+$ was detected, and then the silica support material and a silica sol adhesive having a concentration of 10% were added and slurryed; d) the resultant was extruded through a twin-screw extruder into a cloverleaf-shaped catalyst; and e) the catalyst thus obtained was dried at 120° C. for 6 hours and then calcined at 450° C. for 4 hours, to yield Catalyst A with a pore volume of 0.3 ml/g, an average pore diameter of 5 nm, a specific surface area of 120 m²/g and a crushing strength of 60 N/cm.

A required amount of the obtained Catalyst A was weighted and loaded into the reactor shown in the figure. The first, second and third heat-exchange media used were saturated water steams with different pressures, so as to achieve a temperature difference for controlling the temperature of the catalyst bed in the reactor. In addition, inner and outer tubes configured in a double-tube structure were used. The first partitioning plate was located below the cover plate of the reactor with a distance therefrom of 1/8 of the length of the reactor; the second partitioning plate was located below the first partitioning plate with a distance therefrom of about 1/4 of the length of the reactor; and the third partitioning plate was located below the second partitioning plate with a distance therefrom of about 1/4 of the length of the reactor. The number of the reaction tubes having inner and outer tubes configured in the double-tube structure accounted for 100% of the total number of all reaction tubes in the reactor.

After exchanging heat with the catalyst, the feedstock comprising pure dimethyl oxalate (purchased from Shanghai Guoyao Group, 99.9% purity, the same below) was contacted with Catalyst A under the conditions of a temperature of 220° C., a weight hourly space velocity of 0.5 h⁻¹, a molar ratio of hydrogen to the oxalate of 80:1 and a reaction pressure of 2.8 MPa, to yield an effluent containing ethylene glycol. The results of the reaction are as follows: the conversion of dimethyl oxalate is 100%; and the EG selectivity is 96%.

EXAMPLE 2

Catalyst B comprising 30 parts of Cu, 10 parts of Bi and 1 part of W was prepared according to the steps and under the conditions as described in Example 1, except that the average specific surface area of the silica support material used was 280 m²/g. The resulted catalyst had a pore volume of 0.4 ml/g, an average pore diameter of 6 nm, a specific surface area of 260 m²/g, and a crushing strength of 120 N/cm.

A required amount of the obtained Catalyst B was weighted and loaded into the reactor shown in the figure. The first, second and third heat-exchange media used were saturated water steams with different pressures, so as to achieve a temperature difference for controlling the temperature of the catalyst bed in the reactor. In addition, outer and inner tubes configured in a double-tube structure were used to facilitate the heat exchange of the catalyst. The first partitioning plate was located below the cover plate of the reactor with a distance therefrom of 1/5 of the length of the reactor; the second partitioning plate was located below the first partitioning plate with a distance therefrom of about 1/6 of the length of the reactor; and the third partitioning plate was located below the second partitioning plate with a distance therefrom of about 1/5 of the length of the reactor. The number of the reaction tubes having inner and outer tubes configured in the double-tube structure accounted for 70% of the total number of all reaction tubes in the reactor.

Subsequently, dimethyl oxalate was used as the feedstock under the conditions of a temperature of 250° C., a weight hourly space velocity of 6 h⁻¹, a molar ratio of hydrogen to the oxalate of 100:1 and a reaction pressure of 3.0 MPa of 35%, to achieve a 100% conversion of dimethyl oxalate and an EG selectivity of 95%.

EXAMPLE 3

Catalyst C comprising 30 parts of Cu, 3 parts of Bi and 15 part of W was prepared according to the steps and under the conditions as described in Example 1, except that the support material used was a mixture of silica and alumina. The resulted catalyst had a pore volume of 0.5 ml/g, an average pore diameter of 8 nm, a specific surface area of 230 m²/g, and a crushing strength of 100 N/cm.

A required amount of the obtained Catalyst C was weighted and loaded into the reactor shown in the figure. The first, second and third heat-exchange media used were saturated water steams with different pressures, so as to achieve a temperature difference for controlling the temperature of the catalyst bed in the reactor. In addition, outer and inner tubes configured in a double-tube structure were used to facilitate the heat exchange of the catalyst. The first partitioning plate was located below the cover plate of the reactor with a distance therefrom of 1/7 of the length of the reactor; the second partitioning plate was located below the first partitioning plate with a distance therefrom of about 1/5 of the length of the reactor; and the third partitioning plate was located below the second partitioning plate with a distance therefrom of about 1/3 of the length of the reactor. The number of the reaction tubes having inner and outer tubes configured in the double-tube structure accounted for 20% of the total number of all reaction tubes in the reactor.

Subsequently, diethyl oxalate (purchased from Shanghai Guoyao Group, analytically pure) was used as the feedstock under the conditions of a temperature of 200° C., a weight hourly space velocity of 0.5 h⁻¹, a molar ratio of hydrogen to the oxalate of 100:1 and a reaction pressure of 2.8 MPa, to achieve a 99% conversion of diethyl oxalate and an EG selectivity of 94%.

EXAMPLE 4

Catalyst D comprising 30 parts of Cu, 2 parts of Bi and 8 part of W was prepared according to the steps and under the conditions as described in Example 1, except that the support material was a mixture of silica and alumina. The resulted catalyst had a pore volume of 0.6 ml/g, an average pore diameter of 8 nm, a specific surface area of 300 m²/g, and a crushing strength of 150 N/cm.

A required amount of the obtained Catalyst D was weighted and loaded into the reactor shown in the figure. The first, second and third heat-exchange media used were saturated water steams with different pressures, so as to achieve a temperature difference for controlling the temperature of the catalyst bed in the reactor. In addition, outer and inner tubes configured in a double-tube structure were used to facilitate the heat exchange of the catalyst. The first partitioning plate was located below the cover plate of the reactor with a distance therefrom of 1/4 of the length of the reactor; the second partitioning plate was located below the first partitioning plate with a distance therefrom of about 1/6 of the length of the reactor; and the third partitioning plate was located below the second partitioning plate with a distance therefrom of about 1/3 of the length of the reactor. The number of the reaction tubes having inner and outer tubes configured in the double-tube structure accounted for 60% of the total number of all reaction tubes in the reactor.

Subsequently, diethyl oxalate was used as the feedstock under the condition of a temperature of 240° C., a weight hourly space velocity of 4 h$^{-1}$, a molar ratio of hydrogen to the oxalate of 60:1 and a reaction pressure of 3.8 MPa, to achieve a 99% conversion of diethyl oxalate and an EG selectivity of 96%.

EXAMPLE 5

Catalyst E comprising 45 parts of Cu, 7 parts of Bi and 2 parts of W was prepared according to the steps and under the conditions as described in Example 1, except that the support material was ZSM-5 molecular sieves. The resulted catalyst had a pore volume of 0.4 ml/g, an average pore diameter of 5 nm, a specific surface area of 230 m$^2$/g, and a crushing strength of 80 N/cm.

A required amount of the obtained Catalyst E was weighted and loaded into the reactor shown in the figure. The first, second and third heat-exchange media used were saturated water steams with different pressures, so as to achieve a temperature difference for controlling the temperature of the catalyst bed in the reactor. In addition, outer and inner tubes configured in a double-tube structure were used to facilitate the heat exchange of the catalyst. The first partitioning plate was located below the cover plate of the reactor with a distance therefrom of ¼ of the length of the reactor; the second partitioning plate was located below the first partitioning plate with a distance therefrom of about ⅛ of the length of the reactor; and the third partitioning plate was located below the second partitioning plate with a distance therefrom of about ⅕ of the length of the reactor. The number of the reaction tubes having inner and outer tubes configured in the double-tube structure accounted for 30% of the total number of all reaction tubes in the reactor.

Subsequently, dimethyl oxalate was used as the feedstock under the conditions of a temperature of 230° C., a weight hourly space velocity of 0.3 h$^{-1}$, a molar ratio of hydrogen to the oxalate of 70:1 and a reaction pressure of 2.2 MPa, to achieve a 100% conversion of dimethyl oxalate and an EG selectivity of 95%.

EXAMPLE 6

Catalyst F comprising 20 parts of Cu and 2 parts of Ba was prepared according to the steps and under the conditions as described in Example 1 and using silica as the support material. The resulted catalyst had a pore volume of 0.6 ml/g, an average pore diameter of 6 nm, a specific surface area of 280 m$^2$/g, and a crushing strength of 120 N/cm.

A required amount of the obtained Catalyst F was weighted and loaded into the reactor shown in the figure. The first, second and third heat-exchange media used were saturated water steams with different pressures, so as to achieve a temperature difference for controlling the temperature of the catalyst bed in the reactor. In addition, outer and inner tubes configured in a double-tube structure were used to facilitate the heat exchange of the catalyst. The first partitioning plate was located below the cover plate of the reactor with a distance therefrom of ⅕ of the length of the reactor; the second partitioning plate was located below the first partitioning plate with a distance therefrom of about ¹⁄₁₀ of the length of the reactor; and the third partitioning plate was located below the second partitioning plate with a distance therefrom of about ⅙ of the length of the reactor. The number of the reaction tubes having inner and outer tubes configured in the double-tube structure accounted for 90% of the total number of all reaction tubes in the reactor.

Subsequently, dimethyl oxalate was used as the feedstock under the conditions of a temperature of 230° C., a weight hourly space velocity of 0.2 h$^{-1}$, a molar ratio of hydrogen to the oxalate of 100:1, a reaction pressure of 2.8 MPa, and 14.5% by mass of dimethyl oxalate (and balance of methanol) to achieve a 100% conversion of dimethyl oxalate and an EG selectivity of 98%.

EXAMPLE 7

The same catalyst as prepared in Example 6 was used. A required amount of the obtained Catalyst F was weighted and loaded into the reactor shown in the figure, in which 8 heat-exchange zones equally divided were adopted. All heat-exchange media are saturated water steam with different pressures, so as to achieve a temperature difference for controlling the temperature of the catalyst bed in the reactor. Meanwhile, the number of the reaction tubes having inner and outer tubes configured in the double-tube structure accounted for 80% of the total number of all reaction tubes in the reactor.

Subsequently, dimethyl oxalate was used as the feedstock under the conditions of a temperature of 230° C., a weight hourly space velocity of 0.2 h$^{-1}$, a molar ratio of hydrogen to the oxalate of 100:1, a reaction pressure of 2.8 MPa, and 14.5% by mass of dimethyl oxalate (and balance of methanol) to achieve a 100% conversion of dimethyl oxalate and an EG selectivity of 99%.

EXAMPLE 8

The same catalyst as prepared in Example 6 was used. A required amount of the obtained Catalyst F was weighted and loaded into the reactor shown in the figure, in which 15 heat-exchange zones were adopted with 8 zones being equally divided. All heat-exchange media are saturated water steam with different pressures, so as to achieve a temperature difference for controlling the temperature of the catalyst bed in the reactor. Meanwhile, the number of the reaction tubes having inner and outer tubes configured in the double-tube structure accounted for 60% of the total number of all reaction tubes in the reactor.

Subsequently, dimethyl oxalate was used as the feedstock under the conditions of a temperature of 230° C., a weight hourly space velocity of 0.4 h$^{-1}$, a molar ratio of hydrogen to the oxalate of 100:1, a reaction pressure of 3.0 MPa, and 14.5% by mass of dimethyl oxalate (and balance of methanol) to achieve a 100% conversion of dimethyl oxalate and an EG selectivity of 97%.

COMPARATIVE EXAMPLE 1

An experiment was performed using the catalyst and under the conditions as described in Example 2, except that an adiabatic fixed bed reactor was used. The results of the reaction were as follows: the conversion of dimethyl oxalate was 100% and the EG selectivity was 88%.

What is claimed:
1. A method for production of ethylene glycol using a feedstock comprising an oxalate and a catalyst containing copper and/or a copper oxide, comprising:
    contacting the feedstock with the catalyst in a reactor under conditions of a temperature in a range from about 170 to about 270° C., a weight hourly space velocity of the oxalate in a range from about 0.2 to about 7 h$^-$, a molar ratio of hydrogen to the oxalate in a range from about

20:1 to about 200:1 and a reaction pressure in a range from about 1.5 to about 10 MPa, to produce an effluent containing ethylene glycol, wherein the reactor is a tube-array reactor using partitioned heat exchange and adopting outer and inner tubes configured in a double-tube structure to facilitate heat exchange of the catalyst.

2. The method for production of ethylene glycol according to claim 1, wherein the reaction temperature in the reactor is about 180 to about 260° C.; the weight hourly space velocity of the oxalate is about 0.3 to about 3 h$^-$; the molar ratio of hydrogen to the oxalate is about 50:1 to about 150:1; and the reaction pressure is about 2.0 to about 6.0 MPa.

3. The method for production of ethylene glycol according to claim 1, wherein the catalyst comprises, based on total parts by weight of the catalyst, about 5 to about 80 parts of the copper and/or copper oxide as an active ingredient; about 10 to about 90 parts of at least one of silica, molecular sieve or alumina as a support material; and about 0.01 to about 30 parts of a metal selected from the group consisting of niobium, cerium, bismuth and tungsten, and an oxide thereof as an auxiliary agent.

4. The method for production of ethylene glycol according to claim 1, wherein the catalyst has a pore volume in a range from about 0.1 to about 1 ml/g and an average pore diameter in a range from about 2 to about 12 nm.

5. The method for production of ethylene glycol according to claim 1, wherein the catalyst has a specific surface area in a range from about 100 to about 400 m$^2$/g.

6. The method for production of ethylene glycol according to claim 1, wherein the catalyst has a crushing strength in a range from about 40 to about 180 N/cm.

7. The method for production of ethylene glycol according to claim 1, wherein the catalyst comprises, based on total parts by weight of the catalyst, about 10 to about 60 parts of the copper and/or copper oxide as an active ingredient; about 15 to about 90 parts of at least one of silica or alumina as a support material; and about 0.05 to about 20 parts of metal bismuth and tungsten or an oxide thereof as an auxiliary agents.

8. The method for production of ethylene glycol according to claim 1, wherein the reactor comprises one or more sets of outer and inner tubes configured in a double-tube structure; and at least two heat-exchange zones.

9. The method for production of ethylene glycol according to claim 1, wherein the reactor is mainly composed of a feedstock inlet, a feedstock inlet, a primary gas distribution chamber, a primary gas distribution chamber, a secondary gas distribution chamber, one or more sets of outer tubes and inner tubes, a catalyst bed, a gas collecting chamber, a porous gas-collecting plate and a product outlet, wherein the catalyst bed is divided into a first heat-exchange zone, a second heat-exchange zone and a third heat-exchange zone along the flow direction of the reaction gas; wherein the first heat-exchange zone is connected with a first heat-exchange medium outlet and a first heat-exchange medium inlet; the second heat-exchange zone is connected with a second heat-exchange medium outlet and a second heat-exchange medium inlet; and the third heat-exchange zone is connected with a third heat-exchange medium outlet and a third heat-exchange medium inlet.

10. The method for production of ethylene glycol according to claim 9, wherein the inner tubes are arranged within the catalyst bed and connected with the primary gas distribution chamber or the primary gas distribution chamber located in the gas collecting chamber via an gas inlet connecting hose.

11. The method for production of ethylene glycol according to claim 9, wherein the porous gas-collecting plate is located in the gas collecting chamber and connected with the product outlet.

12. The method for production of ethylene glycol according to claim 9, wherein the first heat-exchange zone and the second heat-exchange are separated by a first partitioning plate, and the second heat-exchange zone and the third heat-exchange zone are separated by a second partitioning plate.

13. The method for production of ethylene glycol according to claim 9, wherein the first partitioning plate is located below the cover plate of the reactor with a distance therefrom in a range from about $1/12$ to about $1/3$ of the a length of the reactor.

14. The method for production of ethylene glycol according to claim 9, wherein the second partitioning plate is located below the first partitioning plate with a distance therefrom in a range from about $1/12$ to about $1/3$ of a length of the reactor.

15. The method for production of ethylene glycol according to claim 9, wherein the first partitioning plate is located below the cover plate of the reactor with a distance therefrom in a range from about $1/10$ to about $1/3$ of a length of the reactor, and the second partitioning plate is located below the first partitioning plate with a distance therefrom in a range from about $1/10$ to about $1/3$ of a length of the reactor.

16. The method for production of ethylene glycol according to claim 13, wherein the first partitioning plate is located below the cover plate of the reactor with a distance therefrom in a range from about $1/10$ to about $1/3$.

17. The method for production of ethylene glycol according to claim 14, wherein the second partitioning plate is located below the first partitioning plate with a distance therefrom in a range from about $1/10$ to about $1/3$.

18. The method for production of ethylene glycol according to claim 15, wherein the first partitioning plate is located below the cover plate of the reactor with a distance therefrom in a range from about $1/8$ to about $1/3$ of the length of the reactor; and the second partitioning plate is located below the first partitioning plate with a distance therefrom in a range from about $1/8$ to about $1/3$ of the length of the reactor.

* * * * *